United States Patent
Wan et al.

(10) Patent No.: US 9,096,744 B2
(45) Date of Patent: Aug. 4, 2015

(54) ANISOTROPIC HYDROGELS

(71) Applicant: THE UNIVERSITY OF WESTERN ONTARIO, London (CA)

(72) Inventors: Wankei Wan, London (CA); Leonardo E. Millon, London (CA); Hadi Mohammadi, London (CA)

(73) Assignee: THE UNIVERSITY OF WESTERN ONTARIO, London, ON (CA)

( * ) Notice: Subject to any disclaimer, the term of this patent is extended or adjusted under 35 U.S.C. 154(b) by 157 days.

(21) Appl. No.: 13/714,675

(22) Filed: Dec. 14, 2012

(65) Prior Publication Data

US 2013/0123371 A1     May 16, 2013

Related U.S. Application Data

(63) Continuation of application No. 11/909,880, filed as application No. PCT/CA2006/000477 on Mar. 30, 2006.

(60) Provisional application No. 60/666,316, filed on Mar. 30, 2005.

(51) Int. Cl.
| | | |
|---|---|---|
| A61F 7/00 | (2006.01) |
| C08L 29/04 | (2006.01) |
| A61L 15/24 | (2006.01) |
| A61L 15/44 | (2006.01) |
| A61L 15/60 | (2006.01) |
| A61L 15/62 | (2006.01) |
| A61L 27/16 | (2006.01) |
| A61L 27/52 | (2006.01) |
| A61L 27/54 | (2006.01) |
| A61L 29/04 | (2006.01) |
| A61L 29/14 | (2006.01) |
| A61L 29/16 | (2006.01) |
| A61L 31/04 | (2006.01) |
| A61L 31/14 | (2006.01) |
| A61L 31/16 | (2006.01) |
| C08F 8/00 | (2006.01) |
| C08J 3/075 | (2006.01) |
| F16L 9/00 | (2006.01) |
| A61B 17/225 | (2006.01) |
| A61F 7/10 | (2006.01) |

(52) U.S. Cl.
CPC ................ *C08L 29/04* (2013.01); *A61L 15/24* (2013.01); *A61L 15/44* (2013.01); *A61L 15/60* (2013.01); *A61L 15/62* (2013.01); *A61L 27/16* (2013.01); *A61L 27/52* (2013.01); *A61L 27/54* (2013.01); *A61L 29/041* (2013.01); *A61L 29/145* (2013.01); *A61L 29/16* (2013.01); *A61L 31/048* (2013.01); *A61L 31/145* (2013.01); *A61L 31/16* (2013.01); *C08F 8/00* (2013.01); *C08J 3/075* (2013.01); *F16L 9/00* (2013.01); *A61B 17/2251* (2013.01); *A61F 7/10* (2013.01); *A61F 2007/0098* (2013.01); *A61L 2300/00* (2013.01); *C08J 2329/04* (2013.01)

(58) Field of Classification Search
CPC .............. A61K 8/34; A61K 8/81; A61F 7/10; A61F 2007/0098
USPC ......................................... 424/400, 422, 484
See application file for complete search history.

(56) References Cited

U.S. PATENT DOCUMENTS

| | | |
|---|---|---|
| 4,323,492 A | 4/1982 | Zimmermann et al. |
| 4,469,837 A | 9/1984 | Cattaneo |
| 4,524,064 A | 6/1985 | Nambu |
| 4,575,551 A | 3/1986 | Fujiyama et al. |
| 4,588,400 A | 5/1986 | Ring et al. |
| 4,656,216 A | 4/1987 | Zimmermann et al. |
| 4,663,358 A | 5/1987 | Hyon et al. |
| 4,851,168 A | 7/1989 | Graiver |
| 4,865,552 A | 9/1989 | Maloney et al. |
| 5,256,418 A | 10/1993 | Kemp et al. |
| 5,336,551 A | 8/1994 | Graiver |
| 5,374,539 A | 12/1994 | Nimni et al. |
| 5,558,861 A | 9/1996 | Yamanaka et al. |
| 5,716,370 A | 2/1998 | Williamson et al. |
| 5,846,213 A | 12/1998 | Wan |

(Continued)

FOREIGN PATENT DOCUMENTS

| | | |
|---|---|---|
| EP | 0860471 | 8/1998 |
| JP | 07216244 | 8/1995 |
| JP | 2004085844 | 3/2004 |
| WO | 9611721 | 4/1996 |
| WO | 0130145 | 5/2001 |
| WO | 2004046229 | 6/2004 |
| WO | 2006102756 | 10/2006 |

OTHER PUBLICATIONS

Makoto Suzuki, "An Artificial Muscle by PVA Hydrogel can Generate High Power Close to Living Skeletal Muscle's", IEEE Engineering in Medicine & Biology Society 11th Annual International Conference, CH2770-6/89/0000-0916, C 1989, IEEE, pp. 0913-0917.

Tatsuo Kaneko et al, "Mechanically Drawn Hydrogels Uniaxially Orient Hhdroxyapatite Crystals and Cell Extension", American Chemical Society, Chem. mater, vol. 16, No. 26, pp. 5596-5601 2004.

Hirai, T. et al., "Effect of Chemical Cross-linking under Elongation on Shape Restoring of Poly(vinyl alcohol) Hydrogel", Journal of Applied Polymer Science, 46 (8), pp. 1449-1451 (1992).

Peppas, N.A. et al., "Poly(vinyl alcohol) hydrogels prepared by freezing-thawing cyclic processing", Polymer, 33(18), pp. 3932-3936 (1992).

(Continued)

*Primary Examiner* — Ruth Davis
(74) *Attorney, Agent, or Firm* — Lynn C. Schumacher; Stephen W. Leonard; Hill & Schumacher

(57) ABSTRACT

Anisotropic hydrogels including poly(vinyl alcohol) and which have physical cross-links so as to form materials which exhibit anisotropic mechanical properties characteristic of soft biological tissues wherein the anisotropic hydrogel may be used for tissue reconstruction and/or replacement including vessels, arteries, valve components, cartilage, ligaments, skin, and other medical uses such as stents, medical phantoms, contact lenses, bandages, and the like.

20 Claims, 14 Drawing Sheets

(56) References Cited

U.S. PATENT DOCUMENTS

| | | | |
|---|---|---|---|
| 5,944,754 | A | 8/1999 | Vacanti |
| 5,958,420 | A | 9/1999 | Jenson |
| 5,989,244 | A | 11/1999 | Gregory |
| 5,990,379 | A | 11/1999 | Gregory |
| 6,117,979 | A | 9/2000 | Hendriks et al. |
| 6,156,531 | A | 12/2000 | Pathak et al. |
| 6,166,184 | A | 12/2000 | Hendriks et al. |
| 6,231,605 | B1 | 5/2001 | Ku |
| 6,372,228 | B1 | 4/2002 | Gregory |
| 6,458,156 | B1 | 10/2002 | Wan et al. |
| 6,855,743 | B1 | 2/2005 | Gvozdic |
| 2001/0044138 | A1 | 11/2001 | Watanabe et al. |
| 2002/0128234 | A1 | 9/2002 | Hubbell et al. |
| 2002/0183848 | A1* | 12/2002 | Ray et al. .................. 623/17.12 |
| 2003/0118560 | A1 | 6/2003 | Kelly et al. |
| 2004/0096509 | A1 | 5/2004 | Hutchens et al. |
| 2005/0106255 | A1 | 5/2005 | Ku |

OTHER PUBLICATIONS

Wan, W.K. et al., "Optimizing the Tensile Properties of Polyvinyl Alcohol Hydrogel for the Construction of a Bioprosthetic Heart Valve Stent.", Journal of Biomedical Materials Research (Applied Biomaterials), vol. 63, pp. 854-861 (2002).

Peppas, N.A. et al., "Structure and Applications of Poly(vinyl alcohol) Hydrogels Produced by Conventional Crosslinking or by Freezing/Thawing Methods", Advances in Polymer Science, vol. 153, pp. 37-65 (2000).

Chen et al., "Boundary layer infusion of heparin prevents thrombosis and reduces neointimal hyperplasia in venous polytetrafluroethylene grafts without systemic anticoagulation.", J. Vascular Surgery, vol. 22, pp. 237-247 (1995).

USPTO Search Report "Anisotropic and hydrogel and PVA" Mar. 20, 2006.

USPTO Search Report "Anisotropic and PVA and hydrogel" Mar. 20, 2006.

Delphion Search Report—Feb. 22, 2005 "Anisotrop* and hydrogel* or polyvinyl alcohol* or poly vinyl alcohol* or poly-vinyl alcohol* or PVA."

Delphion Search Report—Feb. 28, 2005 "(Material or BioMaterial* or Bio-Material*) and (heart or aorta* or vena cava* vein* or artery or arteries or arterial) and anisotrop* or unidimension* or uni-dimension* or mondimension* or mono-dimension or unidirectional or uni-directional or . . . ".

Delphon Search Report—Mar. 1, 2005 "(((polyvinyl alcohol* or poly vinyl alcohol* or oly-vinyl alcohol* or poly-vinyl-alcohol or pva) and . . . ".

Delphion Search Report—Mar. 1, 2005 "(((material* or biomaterial* or bio-material*) and (venous or vascular) and (anisotrop* or unidimension* or uni-dimension* or monodimension* or mono-dimension* or unidectional or uni-directional . . . ".

* cited by examiner

ANISOTROPIC HYDROGELS

FIELD OF THE INVENTION

This invention relates to an anisotropic hydrogel, methods of preparing anisotropic hydrogels and uses thereof.

BACKGROUND OF THE INVENTION

Hydrogels are hydrophilic polymer networks produced from reactions of one or more monomers or by association bonds between chains that can absorb from at least 20% to up to thousands of times their dry weight in water. Hydrogels may be chemically stable or they may disintegrate and dissolve with time. Hydrogels may be classified as either physical or chemical. Physical hydrogels have networks held together by molecular entanglements and/or secondary forces such as hydrogen bonding, van der Waals interactions, ionic or hydrophobic forces. Physical hydrogels are not homogeneous due to regions of high crosslinking density and low water swelling, called clusters, dispersed within low crosslinking density and high water swelling, or hydrophobic or ionic domains that create inhomogeneities. Chemical hydrogels are covalently crosslinked networks, but they may also be generated by crosslinking of water-soluble polymers, or by converting hydrophobic polymers to hydrophilic polymers. Chemical hydrogels are also not homogeneous due to clusters of molecular entanglements. Chain loops and free chain ends also produce network defects in both physical and chemical hydrogels, and they do not contribute to the permanent network elasticity.

An important characteristic of hydrogels is their swelling behaviour in water, since after preparation they have to be in contact with water to yield the final solvated network structure. Poly(vinyl alcohol) (PVA) is a hydrophilic polymer with various characteristics desired for biomedical applications, such as high degree of swelling, uncomplicated chemical structure, rubbery/elastic nature, and non-toxicity.

PVA has a relatively simple chemical formula with a pendant hydroxyl group and a crystalline nature, which allows it to form a solid hydrogel by the crosslinking of the PVA polymer chains. Vinyl alcohol (monomer) does not exist in a stable form and rearranges to its tautomer, acetaldehyde. PVA is produced by free radical polymerization of vinyl acetate to poly(vinyl acetate) (PVAc), and subsequent hydrolysis of PVAc gives PVA.

PVA can be crosslinked using several methods, such as the use of crosslinking chemical agents, using an electron beam or γ-irradiation, or the physical crosslinking due to crystallite formation. For biomedical applications, physical crosslinking has the advantage of not leaving residual amounts of the toxic crosslinking agent, and also provides a hydrogel with higher mechanical strength than those obtained by crosslinking PVA using either chemical or irradiative techniques. In chemical cross-linking, chemical agents that can react with the hydroxyl groups are, for example, glutaraldehyde, ethylaldehyde, terephthalaldehyde, formaldehyde, hydrochloric, boric or maleic acid. Physical crosslinking forms a hydrogel with a network of semi-crystallites of hydrogen bonds filled with solvent.

To date, known methods of producing poly(vinyl alcohol) (PVA) and PVA hydrogel composites provide materials exhibiting the normal characteristic of isotropic mechanical behavior, that is, the mechanical properties of the material are the same regardless of orientation. This is expected due to the random distribution of the polymer chains. The typical tensile behavior for 10% PVA can be seen in FIG. 1, where the mechanical behavior is independent of sample orientation (isotropy).

Most tissues, including cardiovascular tissues, are composite viscoelastic biomaterials displaying mechanical properties with varying degrees of orientation effects. This orientation effect is due to the organization of the structural protein components such as collagen and elastin within the tissue. This organization gives rise to the unique exponential stress-strain relationship exhibited by soft tissues. Up to the present, PVA prepared under specific conditions has displayed some similar mechanical properties to certain soft tissues. However, there is no known synthetic biomaterial that displays anisotropic mechanical behaviour similar to soft tissue.

Even though there are several FDA approved materials for replacement aorta, such as Dacron or e-PTFE, these materials do not posses the same tensile properties as the tissue they are replacing, which results in hemodynamic problems and mismatch of mechanical properties and other problems at the implant/tissue junction.

Therefore, it would be very advantageous to be able to produce a material that displays mechanical properties that are similar to the tissue to be replaced. This would be an important step towards the development of, for example, cardiovascular devices with improved performance and durability.

SUMMARY OF THE INVENTION

A method of preparing hydrogel materials exhibiting anisotropic mechanical properties has been developed.

Accordingly, the present invention includes hydrogel materials and a method of synthesizing hydrogel materials, said materials not only mimicking the exponential tensile properties of soft tissues, but also their orientation effect. This represents a significant step toward creating replacement devices that completely match the mechanical properties of the tissue being replaced.

In one aspect of the invention there is included a hydrogel exhibiting anisotropic properties. In a specific embodiment of the invention the hydrogel is poly(vinyl alcohol) (PVA). The hydrogel may further comprise bioactive agents.

In another aspect of the invention there is included a method of producing an anisotropic hydrogel, comprising:
 a) preparing a solution of poly(vinyl alcohol) with a preselected concentration;
 b) thermally cycling the solution by freezing and thawing to obtain a PVA hydrogel;
 c) stretching the hydrogel; and
 d) thermally cycling the hydrogel at least one more time.

The method may also include adding bioactive agents to the hydrogel.

The present invention further relates to a medical material, device or apparatus comprising an anisotropic hydrogel of the present invention.

The present invention further includes an artificial material for replacing and reconstructing soft tissues comprising an anisotropic hydrogel of the present invention.

Also included within the scope of the present invention is a use of an anisotropic hydrogel of the present invention for tissue replacement, tissue reconstruction, bioagent entrapment, bioagent delivery, preparing ultrasound or radiofrequency thermal therapy transmission pads, preparing substitutes for ice bags, as a denture base, in soft contact lens material, wound covering bandages and phantoms for medical-related uses.

This Summary of Invention lists several embodiments of the invention, and in many cases lists variations and permutations of these embodiments. The Summary is merely exemplary of the numerous and varied embodiments. Mention of one or more specific features of a given embodiment is likewise exemplary. Such embodiment can typically exist with or without the feature(s) mentioned; likewise, those features can be applied to other embodiments of the invention, whether listed in this Summary or not. To avoid excessive repetition, this Summary does not list or suggest all possible combinations of such features.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will be more fully understood from the following detailed description thereof taken in connection with the accompanying drawings, which form a part of this application, and in which.

DETAILED DESCRIPTION OF THE INVENTION

Figure 1:
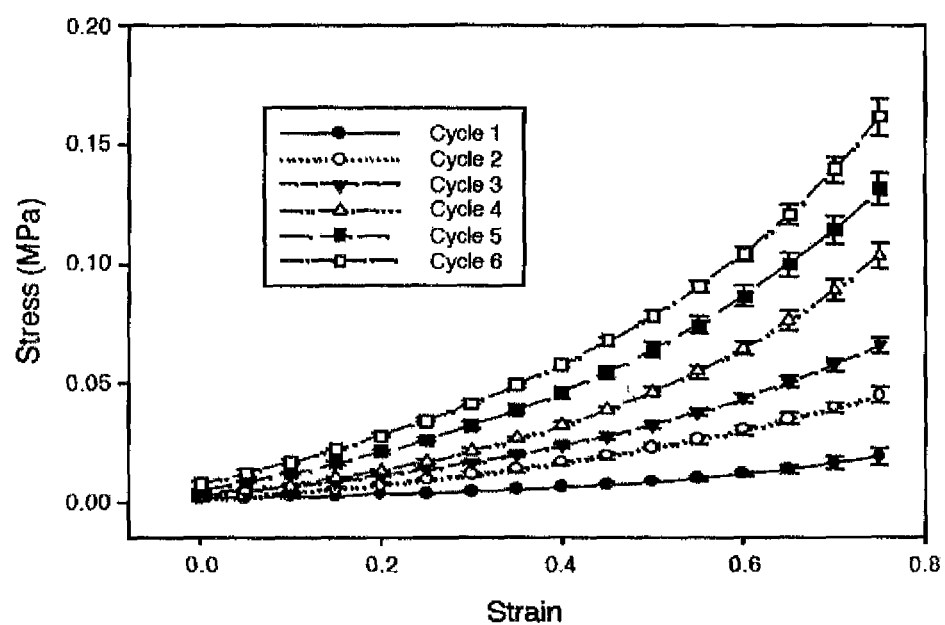
FIG. 1 is a plot showing stress-strain behavior of isotropic 10% PVA (prior art)
Figure 2:
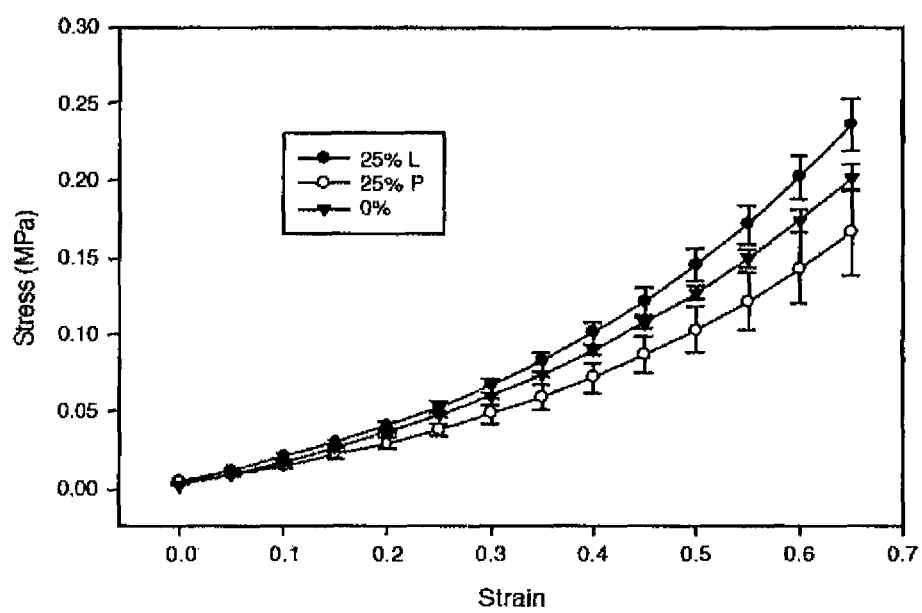
FIG. 2 is a plot showing the effect of 25% initial strain on anisotropy of 10% PVA cycle 6 (longitudinal and perpendicular strips)
Figure 3:
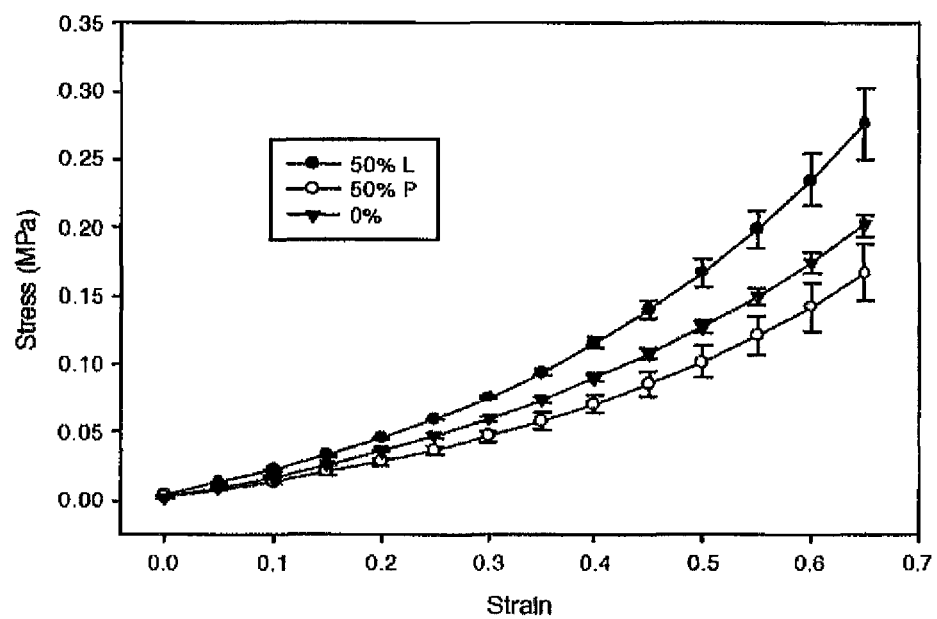
FIG. 3 is a plot showing the effect of 50% initial strain on anisotropy of 10% PVA cycle 6 (longitudinal and perpendicular strips)
Figure 4:
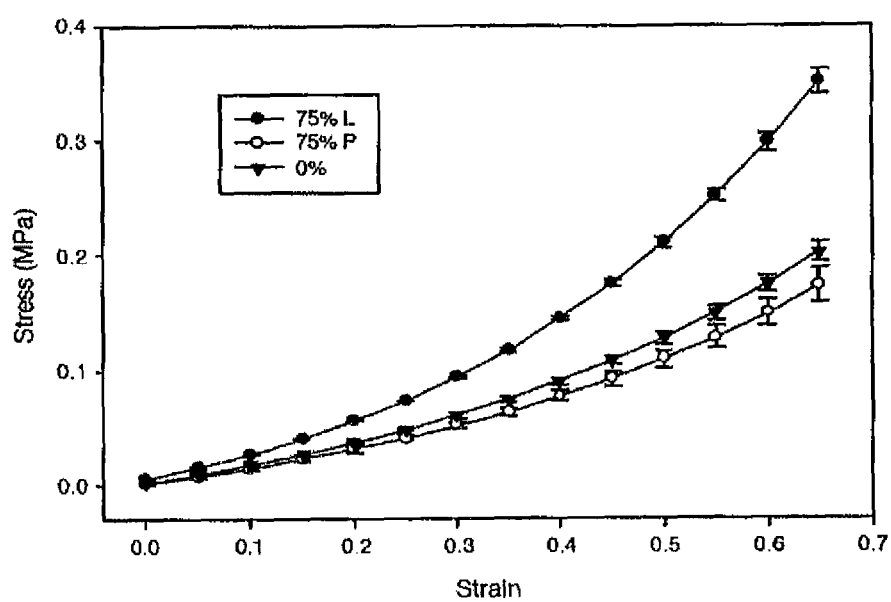
FIG. 4 is a plot showing the effect of 75% initial strain on anisotropy of 10% PVA cycle 6 (longitudinal and perpendicular strips)
Figure 5:
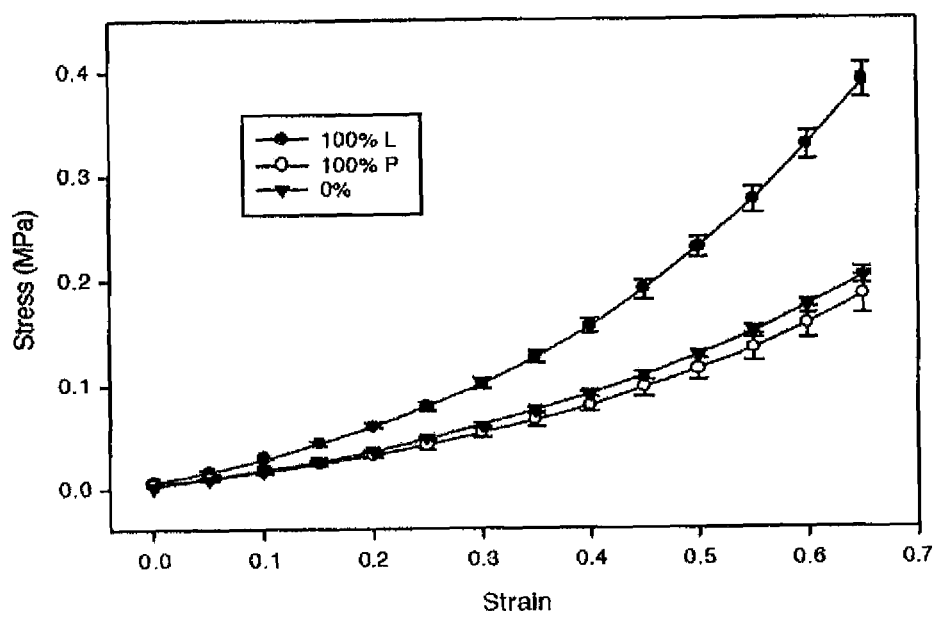
FIG. 5 is a plot showing the effect of 100% initial strain on anisotropy of 10% PVA cycle 6 (longitudinal and perpendicular strips)

A new type of PVA hydrogel has been prepared having properties that mimic the full range of mechanical properties displayed by soft tissues, for example, cardiovascular soft tissues such as vascular grafts, aortic root and heat valve leaflets. Included in the advantageous properties of the PVA hydrogels of the present invention is the fact that, like soft tissues, their mechanical properties are anisotropic, that is they differ depending on orientation.

Accordingly, in one aspect of the invention there is included a hydrogel exhibiting anisotropic properties. In a specific embodiment of the invention the hydrogel is a hydrophilic polymer that forms physical cross-links by thermal cycling. In a further embodiment of the invention, the hydrogel is poly(vinyl alcohol) (PVA). PVA has the unique characteristic of being able to form physical cross-links by thermal cycling, which allows the material to form crystallites using freezing and thawing cycles. The hydrogel may further comprise bioactive agents.

The term "bioactive agents" as used herein includes, but is not limited to one or more of cells, antibodies, cytokines, thrombins, thrombin inhibitors, proteases, anticoagulants, heparin, growth factors, collagen crosslinking inhibitors, matrix inhibitors, glycosaminoglycans and antimicrobial agents, among others. In an embodiment of the invention, the cell cultures are eukaryotic cell cultures, for example, but not limited to vascular cells such as endothelial cells, smooth muscle cells, and fibroblasts and other connective tissue cells It was found that the anisotropic effect produced in the PVA is a function of strain, number of thermal cycles and PVA solution concentration. Accordingly, in another aspect of the invention there is included a method of producing an anisotropic hydrogel, comprising:

a) preparing a solution of poly(vinyl alcohol) with a preselected concentration;

b) thermally cycling the solution by freezing and thawing to obtain a PVA hydrogel;

c) stretching the hydrogel; and d) thermally cycling the hydrogel at least one more time.

In an embodiment of the invention, the solvent for the PVA solution in a) is water, distilled water, isotonic saline or an isotonic buffered saline. Suitably the solvent is distilled water. In a further embodiment of the invention, the concentration of the PVA solution in a) is about 5% to about 25% (w/w), suitably about 7% to about 15%, more suitably about 10%. The PVA solution (suitably with a MW of 146,000 to 186,000, 99+% hydrolyzed) may be prepared by heating, for example at a temperature of about 80° C. to about 100° C., suitably at about 90° C., for an amount of time to achieve the desired solution, for example for about 2 to about 4 hours, suitably about 3 hours.

It is an embodiment of the invention that the PVA solution in a) may be poured into molds of the desired shape of the final device or apparatus.

It is a further embodiment of the invention that thermal cycling of the PVA solution involves cooling the solution from a starting temperature of about 10° C. to about 30° C., suitably about 15° C. to about 25° C., more suitably about 20° C., to finishing temperature of about −10° C. to about −30° C., suitably about −15° C. to about −25° C., more suitably about −20° C., at a rate of from about 0.5° C./min to about 0.05°

C./min, suitably about 0.1° C./min, and holding the solution at the finishing temperature for a suitable length of time, for example from about 0.5 hour to about 2 hour, suitably about 1 hour. To complete one thermal cycle the cooled solution is heated back to the starting temperature at a rate of from about 0.5° C./min to about 0.05° C./min, suitably about 0.1° C./min. The resulting PVA hydrogel is then stretched to a strain of about 25% to about 100%, suitably about 50% to about 90%, more suitably about 70% to about 80%, even suitably about 75%. Following stretching, the PVA hydrogel may optionally be thermally cycled, using the same procedure described above for the first thermal cycle, until a material having the desired mechanical properties are obtained. In an embodiment of the invention the PVA hydrogel is cycled 1-6, suitably 2-5, more suitably 3 times following stretching.

The present invention further includes a method of producing an anisotropic hydrogel, comprising:

a) preparing a solution of poly(vinyl alcohol) with a preselected concentration while heating and mixing for 3 hours at a temperature around 90° C.; and b) thermally cycling the solution by freezing from about 20° C. to about −20° C. at a rate of about 0.1° C./min, holding it at about −20° C. for about one hour, and then thawing it back to 20° C. at a thawing rate of about 0.1°/min.

It has been shown that the mechanical properties of the PVA hydrogels, including elasticity and strength, can be altered by changing the PVA concentration, the number of freeze/thaw cycles, the process thawing rate, the freezing holding time, and the freezing temperature. Increasing the PVA concentration results in hydrogels with higher crystallinity and added stability upon swelling, which increases its tensile strength and tear resistance. The lower the initial concentration of PVA, the fewer the polymer chains in solution, and there may be a lower number of crystalline regions created in the cycled PVA. Increasing the number of freeze/thaw cycles increases the strength and stiffness of the hydrogel by reinforcing existing crystals within the structure. Decreasing the thawing rate of frozen PVA solutions increases the tensile strength. While not wishing to be limited by theory, this may be because the solutions are kept for longer periods at temperatures below 0° C., allowing for increasing movements of polymer chains which results in further entanglements and increased crystallite size and numbers. The freezing holding time also has an effect, with samples frozen up to 10 days giving the most mechanically strong PVA hydrogels. The freezing temperature also has an effect. Again, while not wishing to be limited by theory, the freezing temperature controls the phase equilibria and dynamics, where the lower the temperature of the system, the lower the amount of unfrozen solvent in the liquid regions. Therefore, the lower the temperature, the less opportunity for chain mobility in the polymer rich regions, providing less opportunity for crystallite growth and formation. This may explain why keeping the frozen PVA solutions at −10° C. produces somewhat more rigid hydrogels than those kept for the same period of time at −20 or −30° C. The freezing rate was shown not to have a large effect on the properties of the hydrogel. PVA hydrogels not only have tensile strength and elongation, but also flexibility and elasticity. The ability of PVA hydrogels to recover to their original shape after being deformed to strains of 50% has been shown, which demonstrates their excellent persistence and repeatability of their recovery.

Physical crosslinking allows PVA hydrogels to retain their original shape and be extended up to six times their size. This demonstrates their rubbery and elastic nature and their high mechanical strength. While not wishing to be limited by theory, it has been proposed that the physical cross-linking process is an entropic reordering phenomena. Water is likely to bind to the polymer by hydrogen bonding. When the solution freezes, ice crystals force the polymer chains close to each other forming regions or nuclei of high local polymer concentration. When the material thaws, these nuclei act as crosslinking sites for polymer molecules, which realign and form hydrogen bonds to form crystallites and polymer chain entanglements. The crystalline regions are formed within the polymer rich regions, with further cycling increasing both the size and number of the crystalline regions by repeating the process. On a molecular level, the crystallites of PVA can be described as having a layered structure, with a double layer of molecules held together by hydrogen bonds, while weaker van der Waals forces operate between the double layers. This folded chain structure leads to ordered regions (crystallites) within an unordered, amorphous polymer matrix. The mechanical properties of PVA are very unique compared to other polymers. The stress-strain curves for the polymeric materials are initially linear and then curve towards the strain axis. On the other hand, the PVA curve displays an exponential stress-strain curve similar to the characteristics of soft biological tissues, with the curve shifting towards the stress axis.

PVA materials have been reported to be ideal candidates as biomaterials, due to their high degree of swelling, uncomplicated chemical structure, rubbery/elastic nature, non-toxicity, non-carcinogenicity, and bioadhesive characteristics. Some of the biomedical applications for the materials of the present invention include tissue reconstruction and replacement, bioactive agent entrapment, bioactive agent delivery, an ultrasound or radio frequency thermal therapy transmission pad, as a substitute for an ice bag, as a denture base, soft contact lens material, wound covering bandage, for example, for burn victims, phantoms for medical related use, for example for training and education, ultrasound and magnetic resonance imaging and robotic surgery, among other medical applications.

Accordingly, the present invention, further relates to a medical material, device or apparatus comprising the anisotropic hydrogel of the present invention. It is an embodiment of the invention that the anisotropic hydrogel is prepared using a method of the present invention.

The anisotropic hydrogel of the present invention is particularly useful in surgical and other medical applications as an artificial material for replacing and reconstructing soft tissues in humans and other animals. Soft tissue that may be replaced or reconstructed using the hydrogel of the present invention include, but are not limited to, vascular vessels, such as aorta (large diameter) and coronary arteries (small diameter), heart valve leaflets, heart valve stent, cartilage, ligaments and skin.

Accordingly, the present invention further includes an artificial material for replacing and reconstructing soft tissues comprising the anisotropic hydrogel of the present invention. It is an embodiment of the invention that the anisotropic hydrogel is prepared using a method of the present invention.

The poly(vinyl alcohol) hydrogel of the present invention can also comprise a bioactive agent to provide the hydrogel with suitable physiological properties for it to be used as a soft tissue replacement. The bioactive agent can be chosen based upon the particular application planned for the replacement, and the particular physiological properties required of the replacement in the application involved. Many such bioactive agents would be released gradually from the hydrogel after implantation, and thereby delivered in vivo at a controlled, gradual rate. The hydrogel can thus act as a bioactive agent delivery vehicle, for example, a drug delivery vehicle. Other bioactive agents can be incorporated in to the hydrogel in order to support cellular growth and proliferation on the surface of the material. Bioactive agents which can be included in the material include, for example, one or more of cell lines, antibodies, cytokines, thrombins, thrombin inhibitors, proteases, anticoagulants, heparin, growth factors, collagen crosslinking inhibitors, matrix inhibitors, glycosaminoglycans and antimicrobial agents. Heparins are particularly suitable agents for incorporating into vascular grafts, because of their anticoagulant properties, and thus their ability to inhibit thrombosis on the surface of the hydrogel.

In order to embed bioactive agents into the hydrogel of the present invention any of a pre-sterilized powder, aqueous solution or aqueous suspension can be mixed into the starting sterile poly(vinyl alcohol) solution. After the bioactive agent is incorporated into the poly(vinyl alcohol) solution, it is processed along with the poly(vinyl alcohol) solution according to the method described herein. Bioactive agents can also be introduced into the hydrogel by placing the hydrogel into a bath containing an aqueous solution of the agent and allowing the agent to diffuse into the hydrogel.

Accordingly, the method of the present invention may further comprise adding one or more bioactive agents to the PVA solution in a) or incorporating one or more bioactive agents into the hydrogel after d).

The concentration of the one or more bioactive agents in the mixture may be selected for the particular application involved. For heparin incorporation into a vascular graft, concentrations will typically range from 1 unit/ml to 1,000,000 units/ml. Lower concentrations may be employed to inhibit coagulation on the graft surface, and higher concentrations will be used where local infusion of heparin into the blood is desired to inhibit thrombosis downstream of the graft, as described in Chen et al. (J. Vascular Surgery, v. 22, pp., 237-247, 1995).

The hydrogel of the present invention can be also be used to support the proliferation of eukaryotic cell cultures. Vascular cells such as endothelial cells, smooth muscle cells, and fibroblasts and other connective tissue cells, can thus be incorporated into the hydrogel. Human aortic endothelial cells and human dermal fibroblasts are also compatible with the hydrogels of the present invention. Hydrogels modified by such cell lines are, in turn, especially well adapted for implantation into the human body, and for use as soft tissue replacement parts in the human body. Indeed, replacement parts modified by such cell lines are better able to adapt and adjust to changing physical and physiological conditions in the body, and thereby to prevent any failure of the hydrogel which might otherwise occur. These cellular lines can be incorporated into the hydrogel for example, after it has been produced, via standard cell culture protocol generally known in the art. It is especially effective to culture human aortic endothelial cells and human dermal fibroblasts using direct topical seeding and incubation in cell culture medium.

Also included within the scope of the present invention is a use of an anisotropic hydrogel of the present invention for tissue replacement, tissue reconstruction, bioagent entrapment, bioagent delivery, preparing ultrasound or radiofrequency thermal therapy transmission pads, preparing substitutes for ice bags, as a denture base, in soft contact lens material, wound covering bandages and phantoms for medical-related uses.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

EXAMPLES

Example 1

Method for Producing Anisotropic PVA

A PVA (suitably with a MW of 146,000 to 186,000, 99+% hydrolyzed) solution with the desired concentration in distilled water was prepared by heating while mixing for 3 hours at a temperature around 90° C. The solution was then poured into molds. The molds were then thermally cycled once (cycle 1) by freezing by cooling from about 20° C. to about −20° C. at a rate of about 0.1° C./min, holding at −20° C. for one hour, and then thawing by heating back to 20° C. at a warming rate of about 0.1°/min. This process represents one cycle. The mold was opened and the PVA sheet was stretched to a desired strain in a range of between about 25 to about 100%. The stretched sample was then secured by a custom designed mold. A set of 5 custom design plates were built in order to study the effect of strain and of the number of thermal cycles up to 6 cycles.

Example 2

The Effect of Strain on Anisotropic Mechanical Properties

Figure 6:
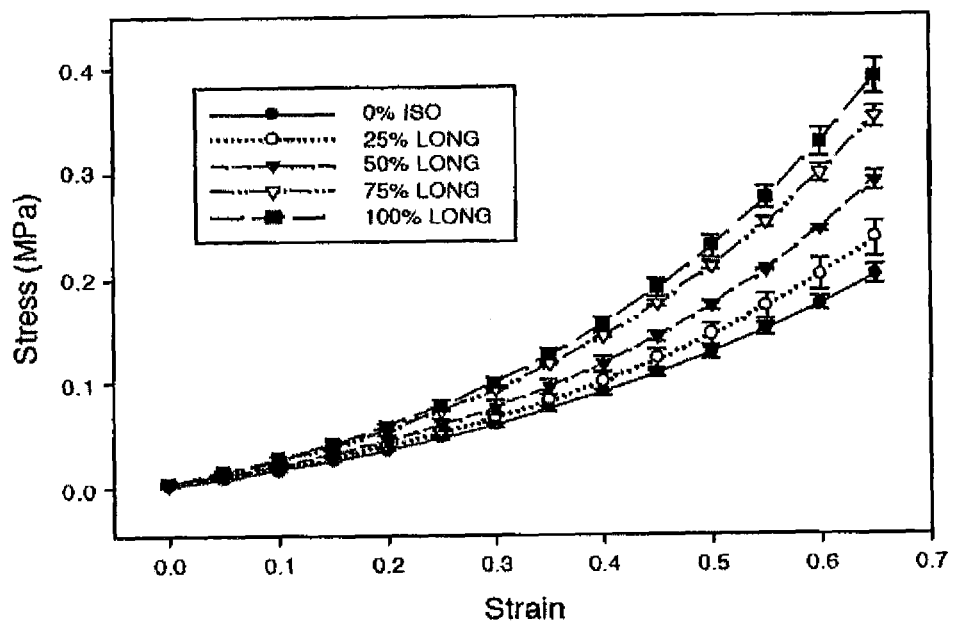
FIG. 6 is a plot showing stress-strain for longitudinal strips as a function of initial strain (cycle 6)
Figure 7:
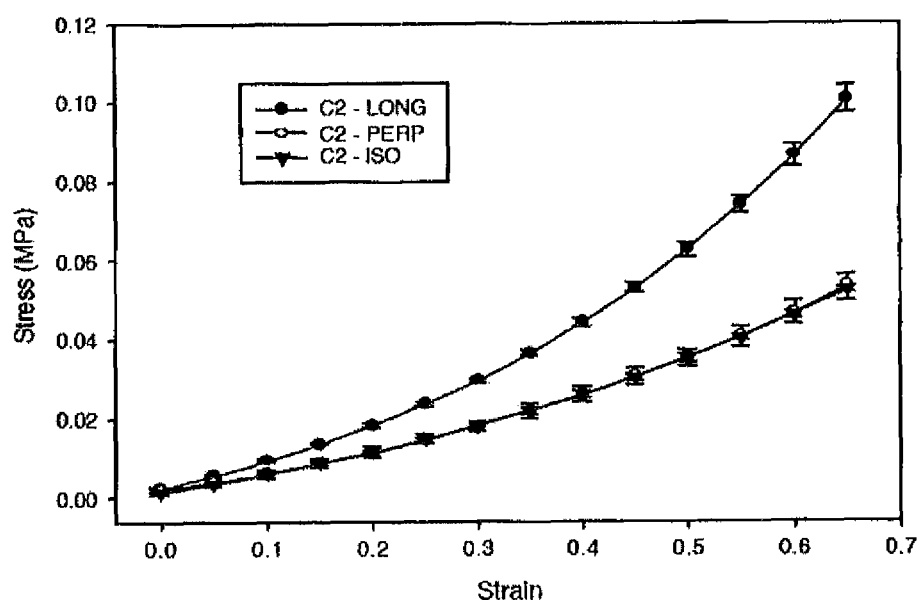
FIG. 7 is a plot showing the effect of 75% strain on a 10% PVA (cycle 2)
Figure 8:
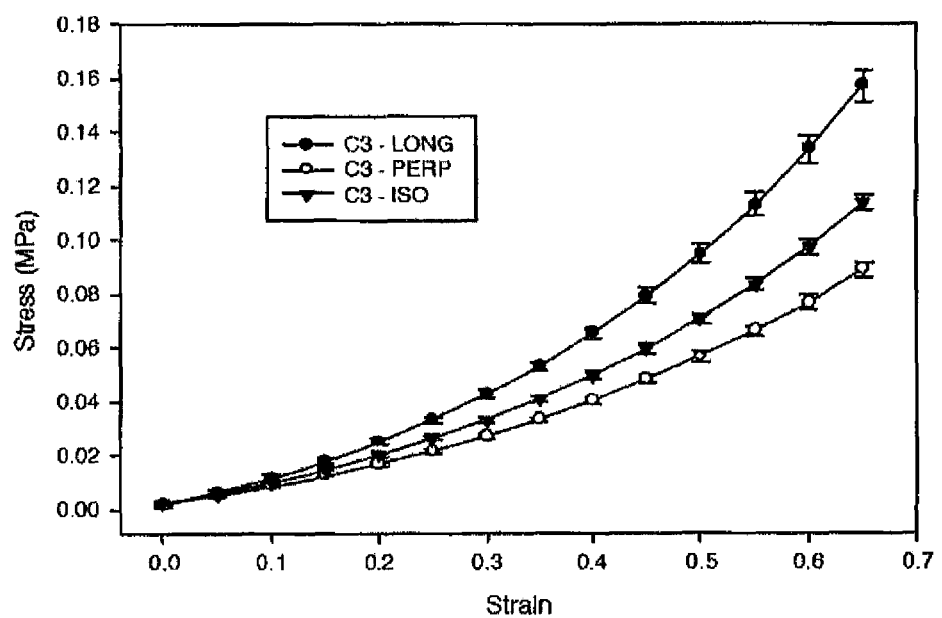
FIG. 8 is a plot showing 75% strain on a 10% PVA (cycle 3)
Figure 9:
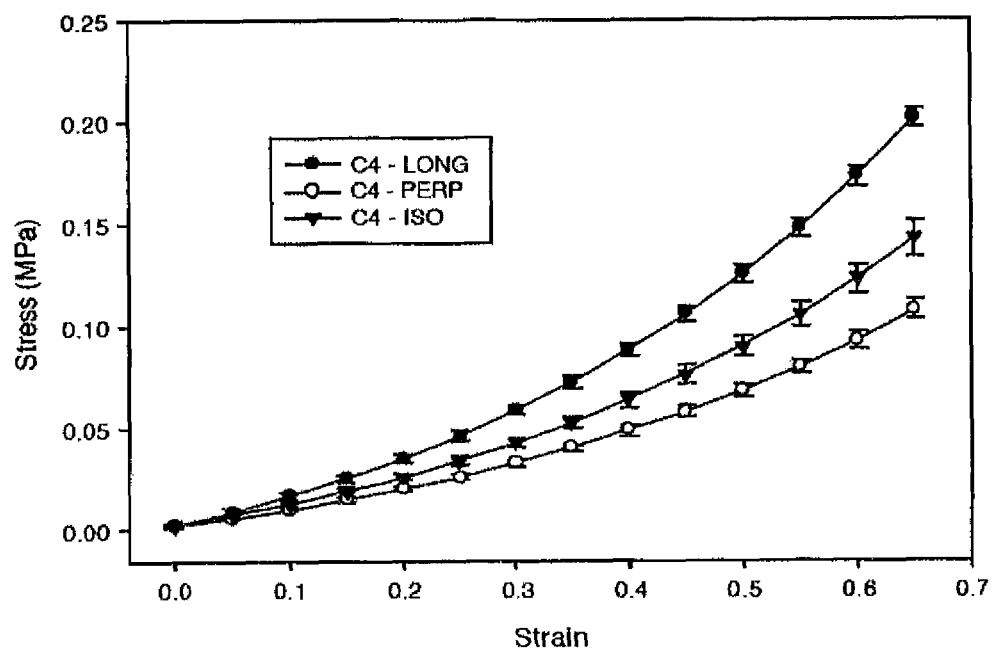
FIG. 9 is a plot showing 75% strain on a 10% PVA (cycle 4)
Figure 10:
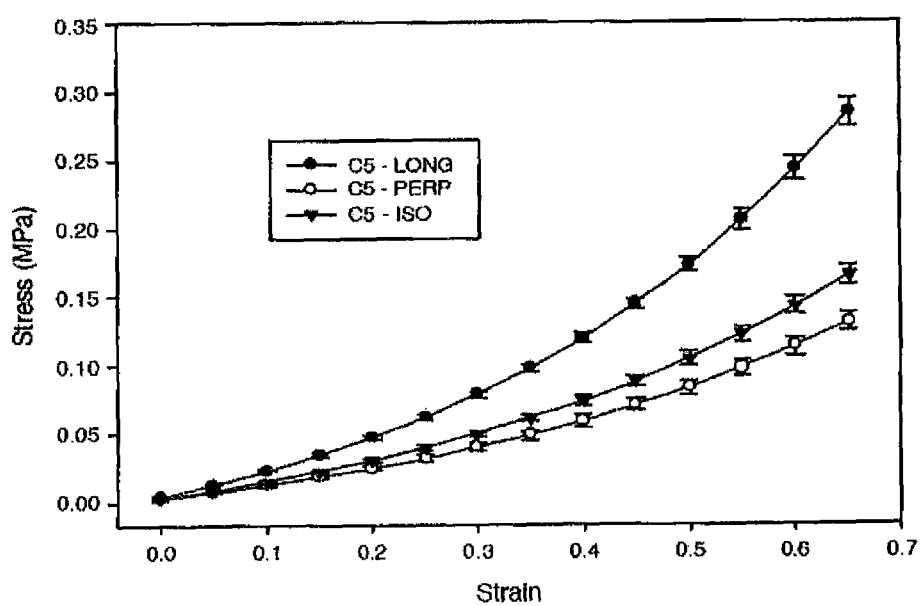
FIG. 10 is a plot showing 75% strain on a 10% PVA (cycle 5)
Figure 11:
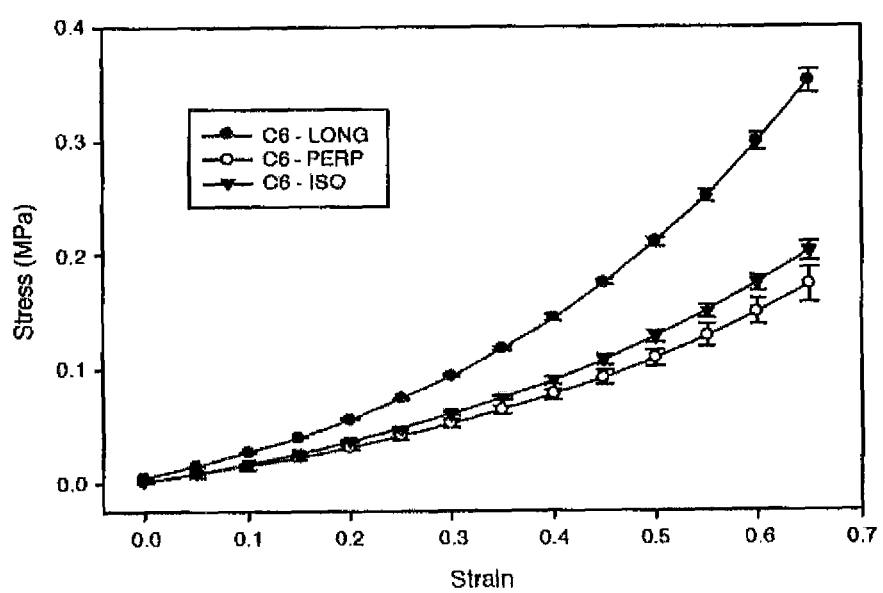
FIG. 11 is a plot showing 75% strain on a 10% PVA (cycle 6)

To study the effect of strain on anisotropic mechanical properties, a 10% PVA solution concentration was used. In this study, five non-stretched samples were physically cross-linked through one freeze-thaw cycle as described in Example 1. One of the samples was left un-stretched and used as control. The remaining four samples were each stretched and secured in the sample molds at 25, 50, 75, and 100% strain. The molds were then closed and placed in a water bath, together with the control, and all samples were cycled up to cycle six, using the freeze-thaw cycling procedure described in Example 1. All the cycle six samples, including the control, were cut in either longitudinal or perpendicular direction to the applied stress. Five samples (n=5) were cut in each direction with dimensions of 25×5 mm². The mechanical testing was performed using an INSTRON™ hydraulic mechanical system. All the samples were tested with a gauge length of ~10 mm while being submerged in a water tank kept at 37° C. The mechanical properties were measured using tensile test (stress-strain). Results of the effect of strain are shown for each strain, together with the results for the isotropic sample (control), in FIGS. 2 to 5. FIG. 6 compares the stress-strain relationship for longitudinal strips as a function of initial strain (through cycle 6). It is seen that there is a clear trend of increase in stiffness of the longitudinal direction as the initial strain is increased from 25 to 100%. Strains higher than 100% were not attempted because in preliminary results it was seen that strains higher than 100% (125%) would show straining marks on the final hydrogel, rendering a non-homogenous surface.

Example 3

The Effect of Number of Thermal Cycles on Anisotropic Mechanical Properties

Figure 12:
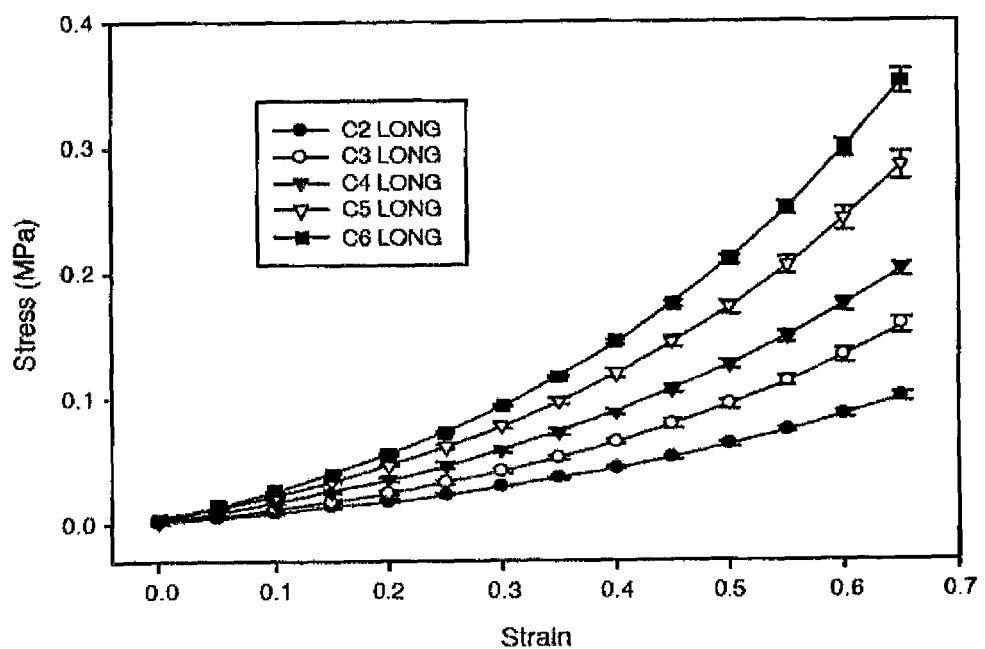
FIG. 12 is a plot showing stress-strain for longitudinal strips as a function of number of cycles

Once again a 10% PVA solution was used in this study. Five samples were physically cross-linked through one freeze-thaw cycle as described in Example 1, at 0% strain. After the first cycle, five samples were then stretched and secured at a strain of 75%. A portion of each sample was retained and cycled through the thermal cycles at 0% strain and were used as controls. All samples were then cycled through cycles two to six. All the samples were cut in either longitudinal or perpendicular direction for tensile testing (n=5). FIGS. 7 to 11 show both the longitudinal and perpendicular strips stress-strain curves as well as the isotropic control data for cycles two to six. Results in FIG. 12 show that in the longitudinal direction, mechanical strength increases as the number of cycles increases. An orientation effect on mechanical strength and the effect of increasing number of thermal cycles can clearly be seen.

Example 4

Comparison of Anisotropic PVA Materials with Porcine Aortic Root

Figure 13:
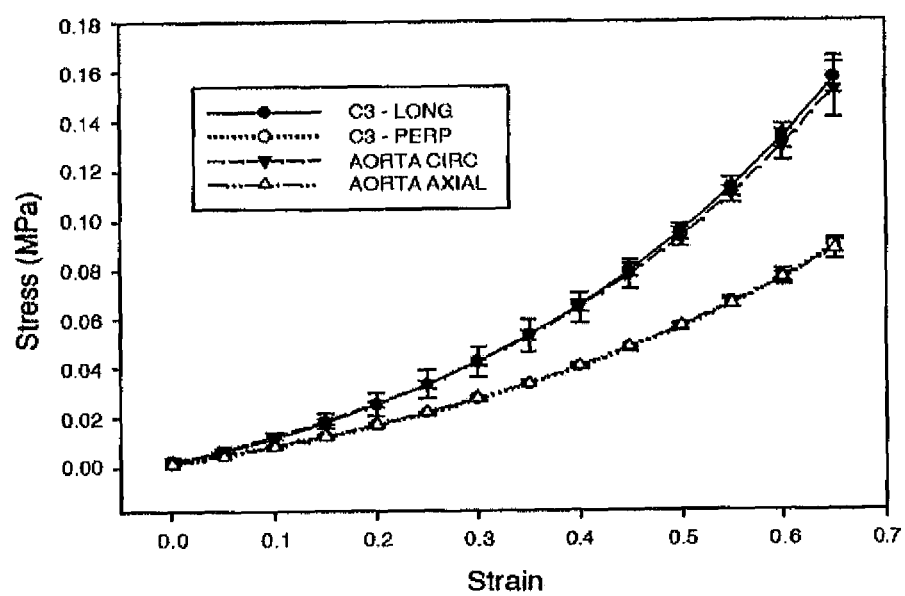
FIG. 13 is a plot showing comparison of 75% strain on anisotropic 10% PVA (cycle 3) and porcine aortic root.
Figure 14:
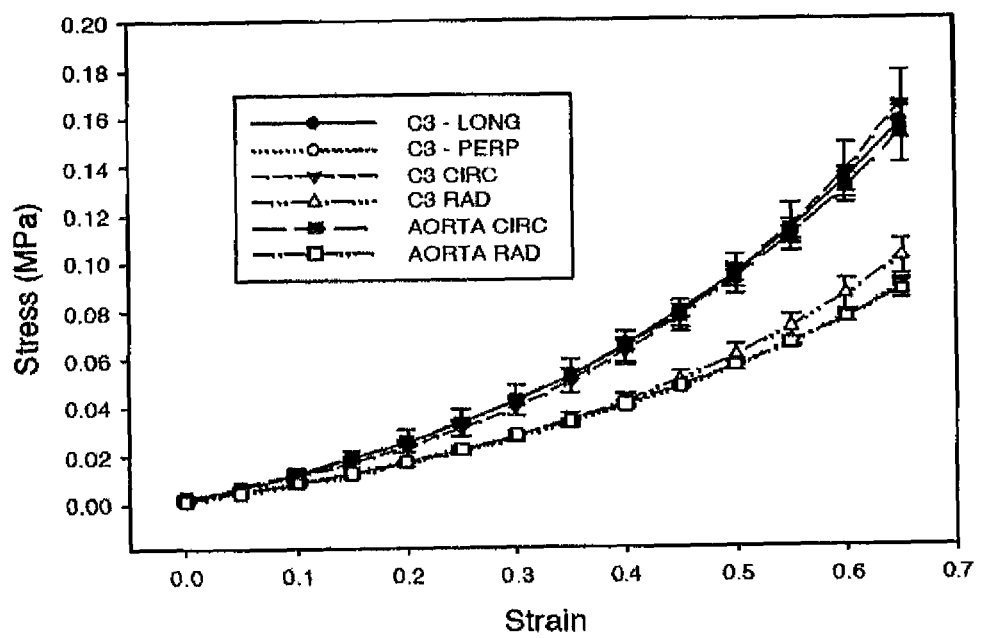
FIG. 14 is a plot showing a comparison of curves of aorta (both directions), the anisotropic PVA sheet sample (75% initial strain—cycle 3), and the anisotropic PVA tubular conduit (75% initial strain—cycle 3).

The success of the method of the present invention is illustrated in FIG. 13. Here results of one of the preparations (75% strain, 10% PVA, cycle 3) is compared to corresponding properties of the porcine aortic root. Good matching of the orientational tensile properties can be seen. To further apply the method of the present invention in a more relevant configuration, an anisotropic PVA tubular conduit was also created, following the same method that was developed for the production of sheets. A tubular PVA conduit cycled once, was stretched onto a larger diameter mold as to introduce 75% strain. This stretched conduit was cycled 2 more times to obtain cycle 3. These conditions were selected since it was shown in FIG. 12 that they provide material that matches the anisotropy of porcine aorta. Samples from the tubular conduits were cut in either circumferential or axial directions (n=5) and mechanically tested. FIG. 14 shows the stress-strain curves of aorta (both directions), the anisotropic PVA sheet sample (75% initial strain—cycle 3), and the anisotropic PVA tubular conduit (75% initial strain—cycle 3). It is clearly seen that good matching of anisotropic properties is obtained. A device that is placed in direct contact with the aortic root made of the new material disclosed herein would not only be able to conform to its movement but would also be substantially stress free. Increased durability is thus expected.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

We claim:

1. An anisotropic hydrogel made up of physical cross-links and exhibiting at least one anisotropic mechanical property, the hydrogel formed by the process comprising the steps of:
   a) preparing a solution of poly(vinyl alcohol) with a preselected concentration;
   b) thermally cycling the solution by freezing and thawing to obtain a PVA hydrogel;
   c) stretching the hydrogel; and
   d) thermally cycling the hydrogel at least one more time while stretching the hydrogel.

2. The anisotropic hydrogel according to claim 1, wherein said anisotropic hydrogel comprises poly(vinyl alcohol).

3. The anisotropic hydrogel according to claim 2 wherein a ratio of the modulus of elasticity in a first direction to the modulus of elasticity in a second orthogonal direction is between approximately 1.4 and 1.9.

4. The anisotropic hydrogel according to claim 2 wherein a ratio of the tangent modulus of elasticity in a first direction to the tangent modulus of elasticity in a second orthogonal direction is between approximately 1.4 and 2.4.

5. The anisotropic hydrogel according to claim 2 wherein said anisotropic mechanical property is characteristic of a soft biological tissue.

6. The anisotropic hydrogel according to claim 5 provided in the form of an anisotropic tubular conduit.

7. The anisotropic hydrogel according to claim 5 wherein said soft biological tissue is selected from the group consisting of vascular vessels, heart valve leaflets, cartilage, ligaments and skin.

8. The anisotropic hydrogel according to claim 7, wherein said vascular vessel is an aorta or coronary artery.

9. The anisotropic hydrogel according to claim 2 wherein said poly(vinyl alcohol) is present in an amount ranging from approximately 5% to about 25%.

10. The anisotropic hydrogel according to claim 2 wherein said poly(vinyl alcohol) is present in an amount ranging from approximately 7% to about 15%.

11. The anisotropic hydrogel according to claim 2 further comprising a bioactive agent.

12. An artificial material having an anisotropic mechanical property resembling that of a soft biological tissue, the artificial material comprising the anisotropic hydrogel according to claim 2.

13. The material according to claim 12 wherein said artificial material is configured for replacing and/or reconstructing soft tissues.

14. The material according to claim 12 wherein said soft biological tissue is selected from the group consisting of vascular vessels, heart valve leaflets, cartilage, ligaments and skin.

15. The material according to claim 14, wherein said vascular vessel is an aorta or coronary artery.

16. The material according to claim 12 wherein said soft biological tissue is a heart valve stent.

17. A medical phantom comprising the anisotropic hydrogel according to claim 2.

18. A surgical training aid comprising an anisotropic hydrogel according to claim 2.

19. A medical material, device or apparatus comprising the anisotropic hydrogel according to claim 2.

20. A contact lens comprising the anisotropic hydrogel according to claim 1.

* * * * *